United States Patent
Leech

(10) Patent No.: US 8,449,893 B2
(45) Date of Patent: May 28, 2013

(54) COMPOSITIONS AND DOSAGE REGIMES COMPRISING A CLOSTRIDIAL VACCINE AND LEVAMISOLE

(75) Inventor: Wayne Frederick Leech, Auckland (NZ)

(73) Assignee: Bayer New Zealand Limited (17012), Auckland (NZ)

( * ) Notice: Subject to any disclaimer, the term of this patent is extended or adjusted under 35 U.S.C. 154(b) by 0 days.

(21) Appl. No.: 13/141,707

(22) PCT Filed: Dec. 15, 2009

(86) PCT No.: PCT/NZ2009/000287
§ 371 (c)(1), (2), (4) Date: Sep. 6, 2011

(87) PCT Pub. No.: WO2010/090532
PCT Pub. Date: Aug. 12, 2010

(65) Prior Publication Data
US 2011/0311589 A1 Dec. 22, 2011

(30) Foreign Application Priority Data
Dec. 24, 2008 (NZ) ........................................ 574018

(51) Int. Cl.
*A61K 39/08* (2006.01)
*A61K 45/00* (2006.01)
*A61K 39/00* (2006.01)
*A61K 39/116* (2006.01)

(52) U.S. Cl.
USPC .................. 424/247.1; 424/239.1; 424/278.1; 424/184.1; 424/203.1

(58) Field of Classification Search
None
See application file for complete search history.

(56) References Cited

FOREIGN PATENT DOCUMENTS
GB 2030043 A * 4/1980

OTHER PUBLICATIONS

Hogarth-Scott et al., Australian Veterinary Journal, 1980; 56: 285-291.*

* cited by examiner

*Primary Examiner* — Vanessa L. Ford
*Assistant Examiner* — Lakia Tongue
(74) *Attorney, Agent, or Firm* — Greer, Burns & Crain, Ltd.

(57) ABSTRACT

A composition and dosage regime including a vaccine and levamisole for the treatment of clostridial diseases and helminthiasis. New methods of administration relating to particular dosage regimes of such a composition are also claimed.

13 Claims, No Drawings

COMPOSITIONS AND DOSAGE REGIMES COMPRISING A CLOSTRIDIAL VACCINE AND LEVAMISOLE

STATEMENT OF CORRESPONDING APPLICATIONS

This application is based on the Provisional specification filed in relation to New Zealand Patent Application Number 574018, the entire contents of which are incorporated herein by reference.

TECHNICAL FIELD

This invention relates to an improved composition and dosage regime.

BACKGROUND ART

Vaccines are widely and frequently used, particularly in the veterinary and farming industries, with a large number of vaccinations for various diseases, infections and other health related issues available.

In the animal health industry in particular, the use of vaccines to protect against clostridial diseases is widespread.

Adverse effects to the wellbeing of animals may result in decreased yields and therefore sale proceeds (either in terms of the live animal, meat or wool) to the owner. Loss of earnings can be considerable and as such, keeping animals healthy is of prime importance to farmers/animal owners.

Anthelmintic preparations are also widely known and used in the animal health industry for the treatment of helminthiasis. One such anthelmintic is levamisole, the laevorotatory isomer of tetramisole. Levamisole is known to be a particularly effective anthelmintic in ruminant animals when administered at a dosage level of approximately 7.5 mg per kg of animal body weight. Dosages that are too low (less than 6 mg per kg of body weight) are ineffective in treating helminthiasis and can encourage resistance in animals, and high dosages have been shown to have a toxic effect on animals. The combination of a vaccine with levamisole was first disclosed in GB 2030043 (1979). This patent describes an acidic injectable composition for the treatment of helminthiasis and prevention of clostridial diseases in animals, comprising a vaccine in combination with tetramisole or levamisole, with no restrictions claimed on effective dosages.

GB 2050830 (1980) discloses a vaccine in combination with levamisole for the use of improving the response of a ruminant animal to the vaccine. GB 2050830 also discloses that when levamisole is issued in combination with a vaccine, it is preferably administered at a dosage rate of approximately 10 to 17 mg per kg of animal body weight.

Following on from the above patent, Schering Plough has produced and marketed a combination levamisole/vaccine composition for a sheep known as Nilvax™.

Nilvax™ is widely used in the animal health industry and is marketed for the treatment of lambs 20 kilograms and over, through to sheep up to 105 kilograms. Nilvax™ provides a composition containing levamisole and a vaccine, with levamisole present at 6.8% levamisole as the free base (equivalent to 10% levamisole phosphate). The dosage regime recommended for Nilvax™ provides animals with a dose of levamisole base from between 17.5 mg per kg for the lightest animal through to 3.78 mg per kg for a heavier animal of 105 kg.

Using these suggested dosages, the amount of levamisole being administered to the animal varies widely, resulting in potentially toxic levels for the smaller animals and ineffective levels of levamisole for the heavier animals. This variation in dosages can be potentially detrimental to the animals and subsequently may result in stock losses for the farmer. Overdosing on levamisole can result in toxicity to the animal and under dosing can be both ineffective in treating helminthiasis and may also increase the risk that the animal will develop resistance to the drug.

It has also been shown by the inventor that known compositions of vaccine and levamisole do not significantly improve antibody levels within animals for all antigens in a vaccine. In Nilvax™, for example, the amount of levamisole administered in conjunction with the vaccine fluctuates widely depending on the weight of the animal. Therefore, any improvement in vaccine response that can be attributed to the presence of levamisole is not maximized, as a consistent amount of levamisole is not provided to all animals across a weight range when using known dosing regimes and compositions. It is therefore an object of the present invention to provide an improved composition and dosage regime that overcomes the above problems or at least provides the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

Further aspects and advantages of the present invention will become apparent from the ensuing description which is given by way of example only.

DISCLOSURE OF INVENTION

According to a first aspect of the invention there is provided a composition including at least 8 w/v % levamisole base and a clostridial vaccine.

According to a further aspect of the invention there is provided a method of treating animals, characterised by the step of administering to the animal a composition including at least 8% w/v levamisole base and a clostridial vaccine.

In a preferred embodiment the animal to be treated may be a ruminant. This is not however intended to be limiting and the composition and the method of treatment may be adapted to suit a variety of animal types.

In preferred aspects of the invention the composition is administered to an animal in need thereof according to the following dosage regime:

| Animal Weight | Amount |
| --- | --- |
| 36-45 kg | 1.8-2.2 mL |
| 46-55 kg | 2.3-2.7 mL |
| 56-65 kg | 2.8-3.2 mL |
| 66-75 kg | 3.3-3.7 mL |
| 76-85 kg | 3.8-4.2 mL |
| 86-95 kg | 4.3-4.7 mL |
| 96-105 kg | 4.8-5.2 mL |
| 106 kg+ | 5.3-5.9 mL. |

Even more preferably, the composition is administered to the animal to the animal according to the dosage regime below:

36-45 kg - 2.0 mL
46-55 kg - 2.5 mL
56-65 kg - 3.0 mL
66-75 kg - 3.5 mL
76-85 - 4.0 mL and
0.5 mL per 10 kg of bodyweight for animals over 85 kg.

This dosage regime has been developed specifically to provide the most effective and efficient dosing of both vaccine and levamisole. This dosage regime has been adapted to be easily administrable to large numbers of animals without the need to make small dosing changes for relatively small changes in animal weight.

According to a further aspect of the invention, there is provided a set of instructions, wherein the instructions include a dosing regime for the administration of a composition including at least 8 w/v % levamisole base and a clostridial vaccine.

In preferred embodiments of the invention the composition includes 10-15% w/v levamisole base.

Throughout this specification the term 'levamisole' should be taken as meaning levamisole phosphate, levamisole hydrochloride, or any other active form of levamisole. The term 'levamisole base' should be taken to mean the amount of free levamisole in the composition.

Levamisole is the active levo-form of tetramisole, and is commonly used as an anthelmintic in the treatment of nematodes, for example stomach worms: *Haemonchus* spp, *Ostertagia* spp, *Trichostrongylus* spp and intestinal worms: *Trichostrongylus* spp, *Cooperia* spp, *Nematodirus* spp, *Bunostomum* spp, *Oesophagostomum* spp, *Chabertia* spp, particularly in veterinary applications. Levamisole is also known to improve the efficacy of vaccines when administered simultaneously.

In a preferred embodiment the levamisole utilised is levamisole phosphate. More preferably, the amount of levamisole phosphate in the composition is 22 mg/mL, which is equivalent to 14.9% levamisole as a free base, and 22% levamisole phosphate.

Reference throughout the rest of this specification will herein be made to levamisole.

As shown by the results of the animal trials outlined in more detail below, a composition of levamisole and a clostridial vaccine is most effective at levels of 22% levamisole phosphate, which is equivalent to 14.9% levamisole base. Compositions containing levamisole dosed at this levels show a marked improvement in the antibody levels of *clostridium tetani, clostridium chauvoei, clostridium septicum, clostridium perfringens* type D and *clostridium novyi* type B when compared to the Nilvax™ in pregnant ewes 14 days after administration. When ranked for effectiveness in promoting an antibody response, the 22% levamisole phosphate composition of the present invention was shown to be overall more effective than Nilvax™, and more effective than a composition containing 15% levamisole phosphate.

The use of 22% levamisole phosphate in the composition, when administered according to the dosage regime of the present invention, results in a consistent administration of levamisole to the animal of between 6.5-8.3 mg/kg/btw, regardless of the weight of the animal. As would be understood by a person skilled in the art, this level of administration is close to the preferred dosage level of levamisole phosphate of 7.5 mg/kg/bwt. 7.5 mg/kg/btw has been shown in the prior art to be the most effective level of levamisole for the treatment of helminthiasis in animals. When compared to the levels of levamisole administered using known formulations and dosage regimes, the novel formulation of the current invention provides a composition that is not only more effective in increasing antibody response in animals, but is also more effective in consistently delivering an effective amount of levamisole for the treatment of helminthiasis in animals.

| Min weight (kg) | Max weight (kg) | Dose Levivax 22% | Dose Nilvax ™ 10% | Levamisole administered mg/kg/bwt Levivax 22% (14.9% base) | Levamisole administered mg/kg/bwt Nilvax ™ 10% (6.8% base) |
| --- | --- | --- | --- | --- | --- |
| 20 | 25 | — | 3.5 | — | 11.9-9.50 |
| 26 | 35 | — | 4.0 | — | 10.4-7.7 |
| 36 | 45 | 2.0 | 4.0 | 8.3-6.6 | 7.5-6.04 |
| 46 | 55 | 2.5 | 4.0 | 8.1-6.8 | 5.91-4.9 |
| 56 | 65 | 3.0 | 4.0 | 8.0-6.6 | 4.8-4.1 |
| 66 | 75 | 3.5 | 4.5 | 7.9-6.9 | 4.6-4.08 |
| 76 | 85 | 4.0 | 4.7 (avg) | 7.8-7.0 | 4.2-3.76 |
| 86 | 90+ | 4.5 | 5.0 | 7.8-7.45 | 3.95-3.78 |

In a preferred embodiment the clostridial vaccine may be an antigenic preparation for any one or more of the following diseases caused by the bacteria of the genus *Clostridium:*
gas gangrene (*Clostridium perfringens* A),
lamb dysentery (*Clostridium perfringens* B),
struck (*Clostridium perfringens* C),
pulpy kidney (*Clostridium perfringens* D),
malignant oedema (*Clostridium septicum*),
blackleg (*Clostridium chauvoei*),
tetanus (*Clostridium tetani*),
black disease (*Clostridium novyi* B),
haemoglobinuria (*Clostridium haemolyticum*),
sordelli infections (*Clostridium sordelli*).

As one skilled in the art would appreciate, any known clostridial vaccine or those still under development may be used singularly or in combination in the present invention.

In the most preferred form, the vaccine of the present invention includes antigenic preparations for *Clostridium perfringens* D, *Clostridium septicum, Clostridium chauvoei, Clostridium tetani* and *Clostridium novyi* B.

The preferred amount of vaccine provided in the present composition follows the recommended dosages provided in the British Veterinary Codex. For example;
*Clostridium Qedematiens* Alpha Antitoxin for horses and cattle 45000 to 75000 and for sheep 9000 to 15000 units.
*Clostridium Perfringens* Type B Antitoxin for the prevention of lamb dysentery subcutaneous injection in sheep 1500 units and for lambs 6000 units.
*Clostridium Perfringens* Type D Antitoxin for the treatment of pulpy kidney disease by subcutaneous injection in sheep 1500 units and for lambs 600 units.

*Clostridium Tetani* Antitoxin prophylactic dose by subcutaneous injection for horses and cattle is not less than 3000 units, for sheep and calves is not less than 500 units and for lambs is not less than 250 units.

The recommended dosages and preparative methods of the various Clostridial vaccines given in BP Veterinary are herein included by way of reference.

It will be understood by a person skilled in the art that it would not be convenient to weight each individual animal before administration and therefore the weight range given is approximate. It should also be understood that the composition and dosage regimes of this invention are not intended for small animals such as lambs (as they receive maternal antibody from the ewe and therefore do not require vaccination when they are very small), but have been developed to ensure that all adult animals receive an efficacious amount of levamisole and vaccine by administration of the novel composition within a set dosage range. The limitations imposed on the dosing regime ensure that animals do not receive a toxic amount of levamisole, an ineffective amount, or an amount that may increase the likelihood of resistance developing. The consistent levels of levamisole administered across the weight spectrum of the adult animal using the dosage regime of the current invention have also proven to be surprisingly effective in increasing the antibody response of animals to a range of different clostridial antigens.

In a further preferred embodiment of the invention there is provided a vaccine and levamisole composition as substantially described above, wherein the composition further comprises at least one additional beneficial substance.

Throughout this specification the term 'beneficial substance' should be taken as meaning any substance from which an animal to which it is administered receives a beneficial effect. The beneficial substance may include for example vitamins, trace elements, minerals, proteins or enzymes to name a few.

More preferably, the beneficial substance is selected from the group including vitamin $B_{12}$, cobalamins, cyanocobalamins and selenium.

Vitamin $B_{12}$ is a cobalt containing vitamin required by cells throughout the body for conversion of ribose nucleotides into deoxyribose nucleotides, a major step in the formation of deoxyribonucleic acid (DNA). Thus it is an essential nutrient for nuclear maturation and cell division. Adult ruminants are not dependent on a dietary source of vitamin $B_{12}$ because bacteria within the rumen synthesise all the vitamin $B_{12}$ needed. However, cobalt is required by the ruminal microorganisms to synthesise this vitamin.

During administration of a vaccine to an animal (which is a significant antigenic challenge), additional administration of an amount of cobalt will enhance utilisation of propionic acid (a volatile free fatty acid) which is a major source of energy. The metabolism of propionic acid is interfered with by a deficiency of vitamin $B_{12}$, and therefore it is a further advantage of the present invention to provide an additional beneficial substance that will ensure vitamin $B_{12}$ is maintained at a healthy level within the animal. Even more preferably, the beneficial substance is vitamin $B_{12}$, preferably at a concentration of 0.05-0.14% or 0.5-1.4 mg/ml.

The composition is preferably manufactured in a readily administrable dosage for subcutaneous or intramuscular use. In a preferred embodiment the composition may be administered via injection.

The composition and dosage regime of the present invention has a number of advantages over the current compositions and dosage regimes known in the art.

The composition of the present invention provides an improved treatment for helminthiasis in animals and an increased clostridial vaccine response in sheep, pregnant ewes and lambs when compared to known compositions.

Specifically, compositions containing 22% levamisole phosphate have been shown to increase the average antibody response to *C. perfringens* Type D, *C. tetani*, *C. chauvoei*, *C. septicum* and *C. novyi* Type B in animals, when compared to known compositions.

The novel composition, when administered using the dosage regime of the present invention provides a therapeutically effective amount of levamisole to animals over a wide range of body weights through administration of lower single dose of a composition than are currently known. Animals over the range of 36 kg-105 kg each receive a dosage of levamisole that is effective in limiting parasite numbers while at the same time increasing the efficacy of the vaccine. The dosage is high enough even with the lighter animals such that the risk of resistance build up is greatly minimised.

Another advantageous factor is that by delivering the vaccine and levamisole composition at lower doses than are previously known, the cost per animal is greatly reduced. This is particularly significant when treating a large number of animals. Wastage is reduced as each animal is receiving the minimal amount of medicament need to provide an effective treatment.

The finding that lower dosage amounts provide a significantly increased antibody response and therefore likelihood of prevention of clostridial disease, together with a more consistent administration of levamisole for the treatment of helminthiasis is both surprising and of considerable advantage to the farmer over known compositions that require higher dosing levels and provide less successful results.

Further advantages are gained by the inclusion of vitamin $B_{12}$ in the composition.

The addition of vitamin $B_{12}$ to the vaccine levamisole composition supplies at least a temporary availability of energy uptake to the animal. This is particularly desirable if the animal is in a compromised state as may be expected following the administration of a vaccine.

Vitamin $B_{12}$ also assists in the production of wool. Strength of fibre can be adversely affected in an animal challenged with an antigenic preparation, and the presence of vitamin $B_{12}$ provides positive effects on the metabolism of the animal.

There is a reduced probability of parasite resistance to levamisole build up. The applicant believes this may be due to an increase in the activity of the immune system which may help and limit parasite numbers. The increased effectiveness of the levamisole in the presence of vitamin $B_{12}$ also ensures that all parasites are killed again, and decreases the possibility of resistance building up.

Examples of the preparation of a medicament according to the present invention are provided below.

EXAMPLES OF PREPARATION OF VACCINE

In general, vaccines for use in the present invention may be prepared according to standards set out in the British Pharmacopoeia (Vet).

Vaccine cultures are grown in deep fermentation tanks. When the toxoid production is complete, the culture is formalised at a suitable pH and the temperature is maintained until the toxoid is sterile and non-toxic.

The cells are removed from the toxoid by sterile centrifugation techniques and the toxoid physically purified, concentrated and stored in sterile containers at 4° C.

The concentrated bulk toxoid is used as the vaccine to stimulate an immune response against the toxin.

The concentrated bulk toxoid is added to sterile aluminium hydroxide adjuvant and made up to volume with sterile normal saline. This is held in pre-sterilised absorption tanks for not less than 24 hours.

Suitable preservatives are then added as will be apparent to those skilled in the art.

EXAMPLES OF COMBINATION MEDICAMENT

A suitable composition according to the invention will comprise a mixture of vaccine, for example clostridial toxoids manufactured in accordance with protocols of the British Pharmacopoeia (Vet), levamisole phosphate at a concentration of 220 mg/mL, one or more preservatives, adjuvants and water for injection.

In variations to the preferred formula, optionally Vitamin $B_{12}$ may be optionally added at a concentration of approximately 0.05-0.14 mg/ml.

The pH is adjusted to preferably 4-5 and most preferably 4.5. It is known that vaccination stimulates the immune. system to produce antibodies 1-2 weeks after injection. In animals such as sheep, to provide adequate cover in previously unvaccinated animals, a first or sensitising dose of the medicament may be boostered by a second injection, for example, 4-6 weeks, and subsequently by annual boosters.

However, in all cases the composition of the invention should be administered in accordance with good veterinary practice, and in particular should be administered suitably according to the particular vaccine regimen which is determined by a veterinarian or other qualified person skilled in the art.

The composition of the present invention was trialled on pregnant ewes and lambs following birth. The results of this study are outlined below.

Animal Trials

A pilot, parallel, blinded, field efficacy study was carried out to assess the efficacy of multivalent clostridial vaccines with different levels of levamisole administered to ewes in late-pregnancy on the antibody titre of ewes and their lambs.

The ability of various test and reference vaccines in composition with levamisole to elevate the level of antibodies to *clostridium tetani, clostridium chauvoei, clostridium septicum, clostridium perfringens* type D and *clostridium novyi* type B antigens in ewes 14 days after treatment and in ewes and lambs 14 days after lambing was determined.

Fifty two ewes bearing a single fetus that had previously been pre-lamb vaccinated with a clostridial vaccine prior to lambing in 2007 were allocated to one of four treatment groups using a randomised block design balancing groups for ewe live weight. The compositions of the present invention are represented by the name "Levivax".

On study day 0, faecal specimens were collected prior to treatment from ewes allocated to receive treatments containing levamisole: negative control (saline), Levivax 15%, Levivax 22% and Nilvax™ (10% levamisole phosphate). Faecal specimens were collected from the same animals 14 days after treatment.

TABLE 1

Animal groups and treatments

| Group | Test/Control substance | n |
|---|---|---|
| 1 | Saline (negative control) | 13 |
| 2 | Levivax (Levamisole phosphate 15% w/v) | 13 |
| 3 | Levivax (Levamisole phosphate 22% w/v) | 13 |
| 4 | Nilvax ™ ™ (Levamisole phosphate 10% w/v) | 13 |
| Total | | 52 |

Blood specimens were collected from all ewes prior to treatment (study day 0), 14 days after treatment (study day 14) and 14 to 21 days after lambing (study day 44-58). Blood specimens were collected from lambs between 14 and 21 days of age. Individual animal serum specimens and sets of serum pooled by treatment group were collected. Individual animal and pooled serum specimens were tested for antibody levels.

Ewes were treated on study day 0 by injecting a single dose subcutaneously into the anterior portion of the neck. The dosing regime of Levivax 15%, Levivax 22%, and Nilvax™ was dependent upon ewe live weight (Table 2).

TABLE 2

Doses dependent on ewe live weight

| Product | Ewe weight range (kg) | Dose (ml) |
|---|---|---|
| Nilvax ™ ™ (10%) | 26-65 | 4.0 |
| | 66-80 | 4.5 |
| | 81-90 | 5.0 |
| | 91-95 | 5.5 |
| | 96-100 | 6.0 |
| Levivax (15%) | 46-55 | 2.2 |
| | 56-65 | 2.8 |
| | 66-75 | 3.3 |
| | 76-85 | 3.9 |
| | 86-95 | 4.4 |
| | 96-105 | 5.0 |
| | 105+ | 5.5 |
| Levivax (22%) | 46-55 | 2.3 |
| | 56-65 | 2.9 |
| | 66-75 | 3.5 |
| | 76-85 | 4.0 |
| | 86-95 | 4.6 |
| | 96-105 | 5.2 |
| | 105+ | 5.8 |

Results

*Clostridium Tetani*

Results of *Clostridium tetani* antibody levels collected on study day 0, 14 and between day 44 and 58 from ewes treated with the negative control, Levivax 15%, Levivax 22% and Nilvax™ products are shown below in table 3.

On study day 0, the mean antibody levels to *C. tetani* antigen did not differ between the negative control and the 3 other treatment groups. On study day 14*, Cl. tetani* antibody responses of ewes in the negative control treatment decreased from pre-treatment levels whereas all other treatments resulted in an increase. Fourteen to twenty-one days after lambing, study days 44-58, ewe antibody responses decreased to levels less than seen at day 0 for ewes in all treatment groups.

On study day 14, ewes treated with Levivax 15% resulted in lower titre than Nilvax™, however Levivax 22% performed better than both Nilvax™ and Levivax 15%.

On study days 44-58, based on Cl. tetani antibody levels, Levivax 15% and Levivax 22% performed similarly to Nilvax™.

TABLE 3

*Clostridium tetani* antibody level (mean ± standard error of the mean) in serum collected on study day 0, 14 and between day 44 and 58 from ewes treated with the negative control, Levivax 15%, Levivax 22% and Nilvax ™ products.

| Treatment | Group | Mean *Cl. tetani* antibody level Study day | | | Mean changes in antibody compared to Day 0 Study day | |
|---|---|---|---|---|---|---|
| | | 0 | 14 | 44-58 | 14 to 0 | 44-58 to 0 |
| Negative control | 1 | 38.8 ± 3.6 | 30.5 ± 4.2 | 21.7 ± 3.4 | −7.0 ± 1.9 | −16.0 ± 2.3 |
| Levivax 15% | 6 | 33.8 ± 4.4 | 51.5* ± 4.5 | 24.6 ± 3.8 | 15.7* ± 4.6 | −7.6 ± 1.5 |
| Levivax 22% | 7 | 43.1 ± 6.1 | 75.1* ± 11.4 | 29.9 ± 7.1 | 33.3* ± 7.2 | −12.2 ± 4.0 |
| Nilvax ™ | 8 | 37.3 ± 3.9 | 69.7* ± 4.6 | 35.2* ± 3.3 | 34.5* ± 4.2 | −2.1* ± 2.9 |

*indicates antibody levels significantly different from the negative control group ($P < 0.05$)

*Clostridium Chauvoei*

*Clostridium chauvoei* antibody levels were collected on study day 0, 14 and between day 44 and 58 from ewes treated with the negative control, Levivax 15%, Levivax 22% and Nilvax™ products. The results are shown in table 4 below.

The mean level of *Cl. chauvoei* antibody in the specimens collected from negative control ewes on day 0 were significantly higher than those collected from ewes in the remaining 3 treatments. On study day 14, antibody levels decreased in the negative control treatment and increased in the remaining 3 treatments. Serum specimens collected between study day 44 and 58 from ewes treated with Levivax 15% and Levivax 22% had higher antibody levels than at pre-treatment (day 0) while ewes in Nilvax™ treatment dropped below these levels.

On study day 14, the level *Cl. chauvoei* antibodies of ewes treated with Levivax 15% and Levivax 22% performed better than Nilvax™, with Levivax 22% performing particularly well.

On study days 44-58, based on the mean level of *Cl. chauvoei* antibody, Levivax 15% and Levivax 22% performed slightly better than Nilvax™.

*Clostridium Septicum*

*Clostridium septicum* antibody levels in serum were collected on study day 0, 14 and between day 44 and 58 from ewes treated with the negative control, Levivax 15%, Levivax 22% and Nilvax™. The results are shown in table 5 below.

Serum antibodies to the *Cl. septicum* antigen on study day 0 were highest in ewes in the negative control treatment but these differences were not significant. On study day 14, the antibody levels of serum collected from ewes in the Levivax 15%, and Levivax 22% treatments were higher than observed in the negative control treatment ($P<0.05$). After lambing, the levels of antibody remained greater than pre-treatment levels for ewes treated with Levivax 15% and Levivax 22%.

On study day 14, the *Cl. septicum* antibody level of ewes treated Levivax 15% and Levivax 22% were significantly higher than those treated with Nilvax™ or negative control.

On study days 44-58, based on mean antibody levels of *Cl. septicum*, Levivax 15% and Levivax 22% performed slightly better than Nilvax™.

Overall, Levivax 15% and Levivax 22% showed significant increases in antibody levels of *Cl. Septicum* between day 0 and days 44-58. Nilvax™ and the negative control both indicated a decrease in the mean amount of serum antibody present between day 0 and days 44-58.

TABLE 4

*Clostridium chauvoei* antibody level (mean ± standard error of the mean) in serum collected on study day 0, 14 and between day 44 and 58 from ewes treated with the negative control, Levivax 15%, Levivax 22% and Nilvax ™ products.

| Treatment | Group | Mean *Cl. chauvoei* antibody level[#] Study day | | | Mean changes in antibody compared to Day 0[#] Study day | |
|---|---|---|---|---|---|---|
| | | 0 | 14 | 44-58 | 14 to 0 | 44-58 to 0 |
| Negative control | 1 | 27.0 ± 3.8 | 20.4 ± 3.4 | 17.2 ± 3.1 | −5.6 ± 1.8 | −8.7 ± 1.3 |
| Levivax 15% | 2 | 15.6 ± 1.6 | 32.0 ± 4.4 | 17.3 ± 1.7 | 16.6* ± 4.3 | 3.0* ± 1.8 |
| Levivax 22% | 3 | 21.2 ± 4.1 | 53.7* ± 9.8 | 23.1 ± 6.7 | 33.0* ± 6.5 | 1.7* ± 3.0 |
| Nilvax ™ | 4 | 15.6 ± 2.3 | 22.3 ± 3.6 | 12.8 ± 1.9 | 8.2* ± 2.4 | −2.8 ± 1.1 |

[#]p-values were based on the analysis of $Log_{10}$ transformed data

*indicates antibody levels significantly different from the negative control group ($P < 0.05$)

TABLE 5

Clostridium septicum antibody level (mean ± standard error of the mean) in serum collected on study day 0, 14 and between day 44 and 58 from ewes treated with the negative control, Levivax 15%, Levivax 22% and Nilvax ™ products.

| Treatment | Group | Mean Cl. septicum antibody level[#] Study day | | | Mean changes in antibody compared to Day 0[#] Study day | |
|---|---|---|---|---|---|---|
| | | 0 | 14 | 44-58 | 14 to 0 | 44-58 to 0 |
| Negative control | 1 | 43.6 ± 5.5 | 36.6 ± 5.0 | 30.3 ± 4.3 | −5.9 ± 4.9 | −11.7 ± 3.4 |
| Levivax 15% | 2 | 29.7 ± 4.3 | 62.1* ± 6.1 | 33.5 ± 4.8 | 32.3* ± 5.1 | 6.8* ± 4.2 |
| Levivax 22% | 3 | 36.7 ± 6.7 | 92.0* ± 10.5 | 38.8 ± 7.8 | 55.2* ± 5.6 | 4.7* ± 3.4 |
| Nilvax ™ | 4 | 32.0 ± 4.5 | 44.9 ± 4.1 | 25.7 ± 3.4 | 16.0* ± 2.8 | −6.3 ± 2.4 |

[#]p-values were based on the analysis of $Log_{10}$ transformed data
*indicates antibody levels significantly different from the negative control group ($P < 0.05$)

*Clostridium Perfringens* Type D

*Clostridium perfringens* type D antibody levels in serum were collected on study day 0, 14 and between day 44 and 58 from ewes treated with the negative control, Levivax 15%, Levivax 22% and Nilvax™. The results are shown in table 6 below.

The level of antibody to the *Cl. perfringens* type D antigen in serum collected on day 0 did not differ between ewes in the 4 treatment groups. On day 14, the levels of antibody decreased slightly in the negative control and increased significantly in all other treatments. After lambing, the level of antibody remained higher than pre-treatment levels in treatment groups Levivax 15% and Levivax 22%.

On study days 44-58, based on the mean antibody levels of *Cl. perfringens* type D, Levivax 15% and Levivax 22% performed similarly to Nilvax™.

TABLE 6

Clostridium perfringens type D antibody level (mean ± standard error of the mean) in serum collected on study day 0, 14 and between day 44 and 58 from ewes treated with the negative control, Levivax 15%, Levivax 22% and Nilvax ™ products.

| Treatment | Group | Mean Cl. perfringens D antibody level Study day | | | Mean changes in antibody compared to day 0 Study day | |
|---|---|---|---|---|---|---|
| | | 0 | 14 | 44-58 | 14 to 0 | 44-58 to 0 |
| Negative control | 1 | 46.8 ± 6.3 | 40.6 ± 7.5 | 28.9 ± 6.3 | −4.3 ± 3.7 | −15.5 ± 3.3 |
| Levivax 15% | 2 | 36.4 ± 4.1 | 76.9* ± 4.0 | 44.9* ± 5.3 | 39.9* ± 4.1 | 10.2* ± 4.3 |
| Levivax 22% | 3 | 40.4 ± 6.4 | 93.1* ± 5.7 | 45.7* ± 6.0 | 51.5* ± 4.6 | 9.5* ± 2.4 |
| Nilvax ™ | 4 | 38.6 ± 4.5 | 71.8* ± 4.2 | 48.2* ± 3.8 | 35.5* ± 3.5 | 9.6* ± 3.6 |

*indicates antibody levels significantly different from the negative control group ($P < 0.05$)

*Clostridium Novyi* Type B

*Clostridium novyi* type B antibody levels in serum were collected on study day 0, 14 and between day 44 and 58 from ewes treated with the negative control, Levivax 15%, Levivax 22% and Nilvax™. The results are shown in table 7 below.

The level of antibody to *Cl. novyi* type B antigen in serum collected on study day 0 did not differ between ewes in all 4 treatments. On study day 14, the level of antibodies in the serum of ewes in the negative control group decreased slightly but increased for ewes in the remaining treatments. After lambing, the levels of antibody remained greater than pre-treatment levels for ewes receiving the Levivax 15% and Levivax 22% treatments.

On study day 14, the level *Cl. novyi* type B antibody indicated that Levivax 15% and performed similarly to Nilvax™, however Levivax 22% performed significantly better, with the mean antibody level being over 4 times that of Nilvax™ or Levivax 15%.

On study days 44-58, based on the antibody levels of *Cl. novyi* type B, Levivax 15% and Levivax 22% were both higher than Nilvax™.

TABLE 7

Clostridium novyi type B antibody level (mean ± standard error of the mean) in serum collected on study day 0, 14 and between day 44 and 58 from ewes treated with the negative control, Levivax 15%, Levivax 22% and Nilvax ™ products.

| Treatment | Group | Mean Cl. novyi antibody level[#] Study day | | | Mean changes in antibody compared to day 0[#] Study day | |
|---|---|---|---|---|---|---|
| | | 0 | 14 | 44-58 | 14 to 0 | 44-58 to 0 |
| Negative control | 1 | 13.0 ± 2.3 | 9.2 ± 1.9 | 5.5 ± 1.3 | −3.3 ± 1.8 | −7.1 ± 1.5 |
| Levivax 15% | 2 | 5.9 ± 1.5 | 12.9 ± 2.9 | 6.5 ± 1.9 | 7.8 ± 2.5 | 2.0* ± 2.0 |
| Levivax 22% | 3 | 13.5 ± 4.1 | 44.7* ± 9.8 | 13.8 ± 6.2 | 31.8* ± 6.3 | 0.8* ± 3.1 |
| Nilvax ™ | 4 | 6.4 ± 1.8 | 10.5 ± 3.5 | 3.3 ± 0.9 | 5.3 ± 2.5 | −3.1 ± 1.2 |

[#]P-values were based on analysis of $Log_{10}$ transformed data
*indicates antibody levels significantly different from the negative control group ($P < 0.05$)

Lamb Serum Results

The level of antibody of the five clostridial antigens was measured in serum collected from lambs between two and three weeks of age. The antibody levels for each species are given in table 8. Lambs born to ewes treated with the negative control product had the lowest level of antibodies to Cl. tetani, Cl. septicum and CL. perfringens type D, however, the antibody levels to both Cl. chauvoei and Cl. novyi type B antigens were lowest in lambs born to ewes treated with Nilvax™.

In lambs the level of Cl. tetani showed Levivax 22% performed similarly to Nilvax™ and EweGuard (P>0.1).

Concentrations of Cl. chauvoei, Cl. septicum, Cl. perfringens and C novyi antibodies indicated treatment with IR 5 produced similar response as treatment with Prolavax 5, Multine 5 in 1 and Ultravac 5 in 1 (P>0.1). In addition, Levivax 15% and Levivax 22% performed similarly to Nilvax™ and EweGuard.

TABLE 8

Level of Cl. tetani, Cl. chauvoei, Cl. septicum, Cl. perfringens type D and Cl. novyi type B antibodies in lamb serum collected at 14 to 21 days of age from lambs born to ewes treated with negative control, Levivax 15%, Levivax 22% and Nilvax ™.

| Treatment | Group | Cl. tetani | Cl. chauvoei | Cl. septicum | Cl. Perfringens D | Cl. Novyi B |
|---|---|---|---|---|---|---|
| Negative control | 1 | 7.3 ± 2.6 | 7.9 ± 2.6 | 14.4 ± 4.0 | 22.1 ± 6.9 | 5.0 ± 1.7 |
| Levivax 15% | 2 | 13.5 ± 3.0 | 13.7* ± 2.6 | 22.9 ± 4.4 | 48.6* ± 5.7 | 6.5 ± 1.6 |
| Levivax 22% | 3 | 18.3 ± 6.9 | 16.8 ± 6.6 | 28.3* ± 6.5 | 44.7* ± 7.2 | 17.0 ± 7.6 |
| Nilvax ™ | 4 | 27.0* ± 4.2 | 6.6 ± 1.8 | 15.4 ± 2.7 | 44.1* ± 3.4 | 4.0 ± 1.6 |

[#] P-values were base on analysis of $Log_{10}$ transformed data
*indicates antibody levels significantly different from the negative control group ($P < 0.05$)

Overall Ranking

The ranking of the ewe and lamb antibody response to treatment indicated that the negative control treatment produced the lowest antibody levels at all time points and for all antibody types in ewes on study day 14 and day 44-58. The lamb ranks indicated that Nilvax™ produced a lower response to Cl. chauvoei and Levivax 15% and 22% both had a higher response to Cl. novyi type B than the negative control treatment at 14 to 21 days of age. A combination of the ranks of the ewe antibody response to the 5 clostridial antigens on day 14 and day 44-58 showed that Levivax 22% had the highest rank followed by Levivax 15% with Nilvax™ 10% in third place. The ranking of the antibody levels of the lambs show that Levivax 22% performed the best followed Levivax 15% then Nilvax™.

Dosage Regime

In a preferred embodiment of the invention a dosage regime is provided that is able to administer an amount of levamisole with a dosage range of between 6.5-8.3 mg/kg/btw. This dosage amount is approximately 30% less than known products such as Nilvax™ when administered according to the preferred dosage regime below:

Dosage Regime Example 1

Dose rate of Levivax 22% and resultant Levamisole Base Conc in mg/kg bwt.

| Min bwt (kg) | Max bwt (kg) | Dose (ml) | Min mg/kg (bwt) | Max mg/kg (bwt) | Average |
|---|---|---|---|---|---|
| 36 | 45 | 2.0 | 8.3 | 6.6 | 7.45 |
| 46 | 55 | 2.5 | 8.1 | 6.8 | 7.15 |
| 56 | 65 | 3.0 | 8.0 | 6.6 | 7.15 |
| 66 | 75 | 3.5 | 7.9 | 6.9 | 7.4 |
| 76 | 85 | 4.0 | 7.8 | 7.0 | 7.4 |
| 85+ | | 0.5 mL/10 kg | | | |

As would be understood by a person skilled in the art, individual dosages given to animals may vary slightly as shown above. For the purposes of commercializing such a product as described herein it is more effective to market a dosage regime that increases in set increments of certain numbers. For example, the dosage example provided in example two is that used in the animal trials conducted in support of the current invention. However, the dosage regime outlined in example one provides a clearer dosing system for the user, while still administering the required amount of vaccine and levamisole phosphate to the animals. As such, small variations in the dosing regime are considered to be included within the scope of this invention.

Aspects of the present invention have been described by way of example only and it should be appreciated that modifications and additions may be made thereto without departing from the scope thereof as defined in the appended claims.

I claim:

1. A composition comprising: 10-15% w/v levamisole base and a clostridial vaccine.

2. The composition of claim 1, wherein the levamisole is present in the form of levamisole phosphate.

3. The composition of claim 2, wherein the composition includes 22 mg/mL levamisole phosphate.

4. The composition of claim 2 wherein the amount of levamisole phosphate in the composition is 22 w/v%.

5. The composition of claim 1, wherein the clostridial vaccine is an antigenic preparation for one or more of the diseases selected from the group including gas gangrene, lamb dysentery, struck, pulpy kidney, malignant oedema, blackleg, tetanus, black disease, haemoglobinuria and/or sordelli infections.

6. The composition of claim 5, wherein the clostridial vaccine includes vaccine for Clostridium perfringens Type D, Clostridium tetani, Clostridium chauvoei, Clostridium septicum and Clostridium novyi Type B.

7. The composition as claimed in claim 1, wherein the composition includes at least one beneficial substance selected from the group including cobalamins, cyanocobalamins and selenium.

8. The composition of claim 7, wherein the beneficial substance is vitamin B12, at a concentration of 0.5-1.4 mg/ml.

9. The composition as claimed in claim 1, wherein the composition is injectable.

10. A method of treating animals for one or more of the diseases selected from the group including gas gangrene, lamb dysentery, struck, pulpy kidney, malignant oedema, blackleg, tetanus, black disease, haemoglobinuria and/or sordelli infections, comprising the step of administering to the animal a composition comprising: 10-15% w/v levamisole base and a clostridial vaccine.

11. The method of claim 10, wherein the animal to be treated is a ruminant.

12. The method of claim 10, wherein the composition is administered to an animal in need thereof according to the following dosage regime: in the amount of 1.8-2.2 ml per 36-45 kg of animal weight, 2.3-2.7 mL per 46-55 kg of animal weight, 2.8-3.2 mL per 56-65 kg of animal weight, 3.3-3.7 mL per 66-75 kg of animal weight, 3.8-4.2 mL per 76-85 kg of animal weight, 4.3-4.7 mL per 86-95 kg of animal weight, 4.8-5.2 mL per 96-105 kg animal weight, 4.8-5.2 mL per 96-105 kg animal weight, and 5.3-5.9 mL per 106 kg of animal weight.

13. The method of claim 10, wherein the composition is administered to the animal according to the following dosage regime: in the amount 2.0 ml per 36-45 kg of animal weight, 2.5 mL per 46-55 kg of animal weight, 3.0 mL per 56-65 kg of animal weight, 3.5 mL per 66-75 kg of animal weight, 4.0 mL per 76-85 kg of animal weight, and 0.5 mL per 10kg of bodyweight for animals over 85 kg.

* * * * *